United States Patent
Lemus et al.

(10) Patent No.: US 7,091,042 B2
(45) Date of Patent: Aug. 15, 2006

(54) VARIABLE RESISTANCE STERILIZATION PROCESS CHALLENGE DEVICE AND METHOD

(75) Inventors: Anthony Lemus, Villa Park, CA (US); Debra Timm, Foothill Ranch, CA (US)

(73) Assignee: Ethicon, Inc., Somerville, NJ (US)

( * ) Notice: Subject to any disclaimer, the term of this patent is extended or adjusted under 35 U.S.C. 154(b) by 580 days.

(21) Appl. No.: 10/002,038

(22) Filed: Nov. 2, 2001

(65) Prior Publication Data

US 2003/0087441 A1 May 8, 2003

(51) Int. Cl.
- A61L 2/16 (2006.01)
- A61L 2/28 (2006.01)
- A61L 12/08 (2006.01)

(52) U.S. Cl. ............... 436/1; 422/1; 422/102; 422/104

(58) Field of Classification Search .......... 436/1, 436/2; 422/26–28, 1, 102, 104; 435/31, 435/32, 2

See application file for complete search history.

(56) References Cited

U.S. PATENT DOCUMENTS

| | | |
|---|---|---|
| 4,580,682 A | 4/1986 | Gorski et al. |
| 4,596,696 A | 6/1986 | Scoville, Jr. |
| 4,636,472 A | 1/1987 | Bruso |
| 4,743,537 A | 5/1988 | McCormick et al. |
| 4,885,253 A | 12/1989 | Kralovic |
| 5,066,464 A | 11/1991 | Augurt |
| 5,073,488 A | 12/1991 | Matner et al. |
| 5,217,901 A | 6/1993 | Dyckman |
| 5,344,017 A | 9/1994 | Wittrock |
| 5,418,167 A | 5/1995 | Matner et al. |
| 5,435,971 A | 7/1995 | Dyckman |
| 5,620,656 A | 4/1997 | Wensky et al. |
| 5,727,684 A | 3/1998 | Webb et al. |
| 5,739,004 A | 4/1998 | Woodson |
| 5,750,184 A | 5/1998 | Imburgia |
| 5,801,010 A | 9/1998 | Falkowski et al. |
| 5,824,553 A | 10/1998 | McCormick et al. |
| 5,830,683 A | 11/1998 | Hendricks et al. |
| 5,866,356 A | 2/1999 | Albert et al. |
| 5,872,004 A | 2/1999 | Bolsen |
| 5,895,627 A | 4/1999 | Khachatoorian |
| 5,942,408 A | 8/1999 | Christensen et al. |
| 5,955,025 A | 9/1999 | Barrett |
| 5,955,296 A | 9/1999 | Roll |
| 5,989,852 A | 11/1999 | Hendricks et al. |
| 6,063,631 A | 5/2000 | Ignacio |
| 6,156,267 A | 12/2000 | Pai |
| 6,218,189 B1 | 4/2001 | Antonoplos et al. |
| 6,267,242 B1 | 7/2001 | Nagata et al. |
| 6,325,972 B1 * | 12/2001 | Jacobs et al. ............. 422/33 |

FOREIGN PATENT DOCUMENTS

| | | |
|---|---|---|
| WO | WO 97 12637 A | 4/1997 |
| WO | WO 01 13964 A | 3/2001 |

* cited by examiner

Primary Examiner—Jill Warden
Assistant Examiner—LaToya C. Younger

(57) ABSTRACT

A sterilization process challenge device has a sterilization indicator contained within a container; and a variable diffusion restriction into said container.

16 Claims, 4 Drawing Sheets

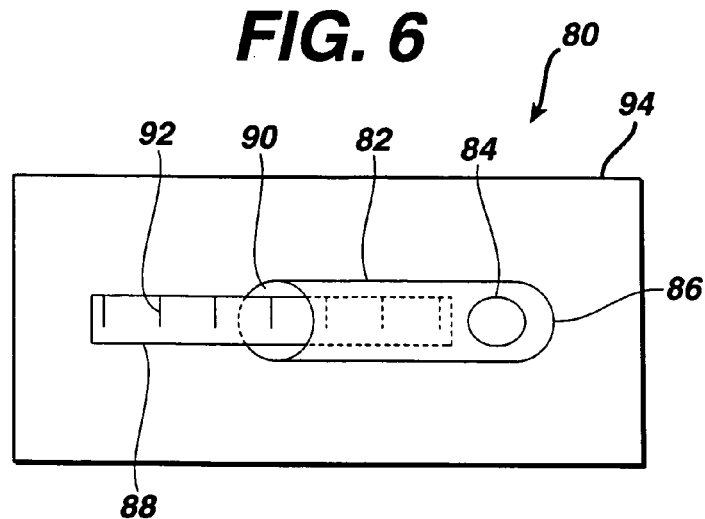
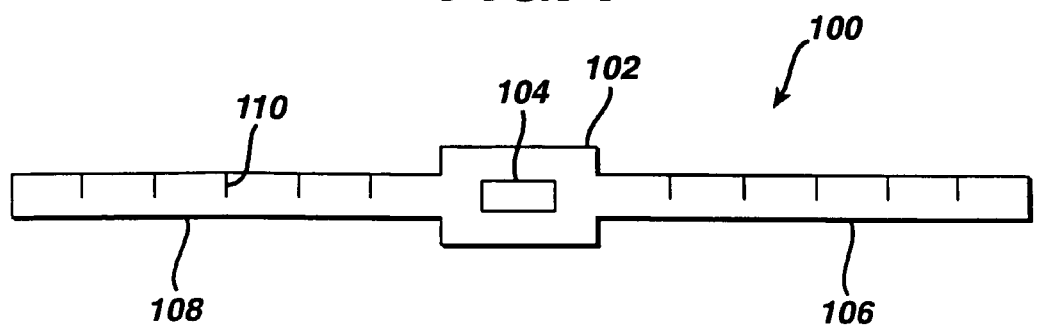

VARIABLE RESISTANCE STERILIZATION PROCESS CHALLENGE DEVICE AND METHOD

FIELD OF THE INVENTION

The present invention relates to a process challenge device and method for determining the efficacy of a sterilization procedure.

BACKGROUND

Medical instruments are typically sterilized prior to use. Many methods are employed, including steam sterilization, hydrogen peroxide, vapor phase sterilization, either with or without a gas plasma and ethylene oxide (EtO). Each of these methods relates to a certain extent on the diffusion of fluid, primarily gaseous, sterilants into contact with the instruments and devices to be sterilized.

Typically, such instruments and devices are packaged within containers or pouches having a semi-permeable barrier, which allows transmission of the sterilizing fluid but prevents admission of contaminating organisms. Packaging of the instruments in this fashion creates a diffusion restriction somewhat inhibiting passage of the sterilizing fluid to the device or instrument. In addition, some devices and instruments have diffusion-restricted spaces therein; for example, endoscopes typically have long narrow lumen. The sterilizing fluid must diffuse into this long narrow lumen to effect sterilization therein. In addition to diffusion restrictions, the quantity of devices to be sterilized during one process, and the amount of absorbent material in proximity thereto all affect how the sterilizing fluid travels to and contacts the instruments to effect sterilization. A sufficient amount must remain in contact with the instrument for a sufficient period of time to achieve a desired level of sterilization.

To insure that proper sterilization has been achieved, it is typical to include some indicator of the sterilization process in proximity to the devices or instruments to be sterilized during the process. For instance, a biological indictor having a predetermined quantity of micro-organisms can be placed within a sterilization chamber if the device is to be sterilized and, after the process is complete, it can be cultured to determine whether any of the micro-organisms have survived. Biological indicators have evolved into designs in which a source of growth media in a frangible container is located adjacent to a quantity of microorganisms and after the sterilization procedure is completed, the frangible container is broken to release the growth media and culture any remaining living organisms. Typically, color indication technology is included to show a color change in the presence of living organisms. Alternatively, an enzyme indicative of the organism viability may be detected. Examples of such devices are shown in U.S. Pat. Nos. 5,830,683 and 5,418,167, hereby incorporated by reference.

To more accurately replicate a challenge of diffusing a sterilant fluid into contact with the device during an actual sterilization procedure, it has sometimes been the practice to place a biological indicator inside of a challenge device having a diffusion restriction, such as a long tortuous path. U.S. Pat. Nos. 5,895,627 and 5,872,004 illustrate examples of such challenge devices, and are incorporated herein by reference.

SUMMARY OF THE INVENTION

A sterilization process challenge device according to the present invention comprises a sterilization indicator contained within a container and a variable diffusion restriction into the container.

The sterilization indicator can be a biological indicator or a chemical indicator indicative of a chemical sterilant.

The variable diffusion restriction can comprise a diffusion path into the container which can comprise an adjustable covering for the path to block or unblock portion of the diffusion path. In one embodiment of the invention, the container comprises a first member and second member disposed in telescoping relation with the openings disposed on the first member and the second member forming the adjustable covering.

The diffusion path can comprise a plurality of openings, which can be different in size. At least one opening is preferably covered with a removable covering. Rather than, or in addition to multiple openings, the diffusion path can comprise a slot, portions of which can be covered or uncovered to vary the diffusion resistance.

The diffusion path can comprise a long narrow path, wherein the diffusion path can be adjusted by trimming the length of the path. The diffusion path can comprise two or more materials wherein the materials have different capabilities to retain sterilant. The diffusion path can comprise a sterilant absorber such that the amount of sterilant diffusing to the indicator can be adjusted by the type or the size of the absorber.

A method for assessing the sterilization efficacy of a sterilization process according to the present invention comprises the steps of: placing a sterilization process challenge device in proximity to a device to be sterilized during the sterilization process, the sterilization process challenge device comprising a container, a sterilization indicator within the container, an opening into the container and an adjustable diffusion restriction at the opening; assessing a feature of a load of one or more devices to be sterilized in the sterilization process; adjusting the amount of diffusion restriction provided by the diffusion restriction based upon the feature of the load; and indicating the sterilization efficacy with the indicator.

The step of adjusting the amount of diffusion restriction can comprise adjusting an area of the opening into the container, such as by covering or uncovering the opening into the container. The opening can comprise a plurality of apertures in a wall of the container.

The diffusion restriction can comprise a path into the container and the step of adjusting the amount of diffusion restriction can comprise adjusting the length of the path.

The step of adjusting the diffusion restriction can comprise adjusting an amount of absorbent material placed adjacent the indicator.

The indicator can indicate whether a reference organism remains viable or whether a sufficient amount of a sterilizing gas was present during the sterilization process.

BRIEF DESCRIPTION OF THE DRAWINGS

FIG. 6 is a top plan view of a sixth embodiment of a process challenge device according to the present invention; and FIG. 7 is a top plan view of a seventh embodiment of a process challenge device according to the present invention.

DETAILED DESCRIPTION

Figure 1:
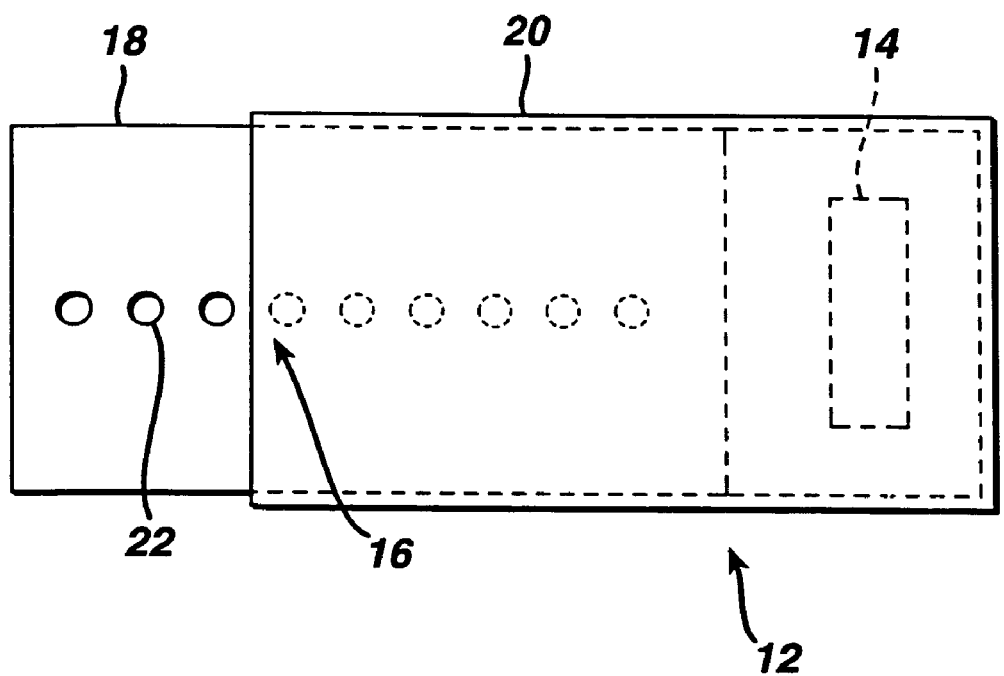
FIG. 1 is a top plan view of a challenge device according to the present invention.

FIG. 1 illustrates a process challenge device 10 according to the present invention. It comprises an enclosure 12 containing an indicator 14 and diffusion restricted passage 16 leading into the enclosure 12. The enclosure 12 comprises a first open-ended body 18 and a second open-ended body 20 disposed in telescoping relation to one another. The diffusion restricted passage 16 comprises a variety of apertures 22 in the first body 18 which are selectively covered and uncovered by the second body 20 as the first and second body 18 and 20 are telescoped in relation to one another. When all of the apertures 22 are uncovered, it is much easier for sterilizing fluid to diffuse into the enclosure 12 and contact the indicator 14 than when only a few of the apertures 22 are uncovered. Accordingly, the challenge device 10 provides an easy and simple means for providing a process challenge, which can be adjusted in accordance with the needs of a particular sterilization process.

Figure 2:
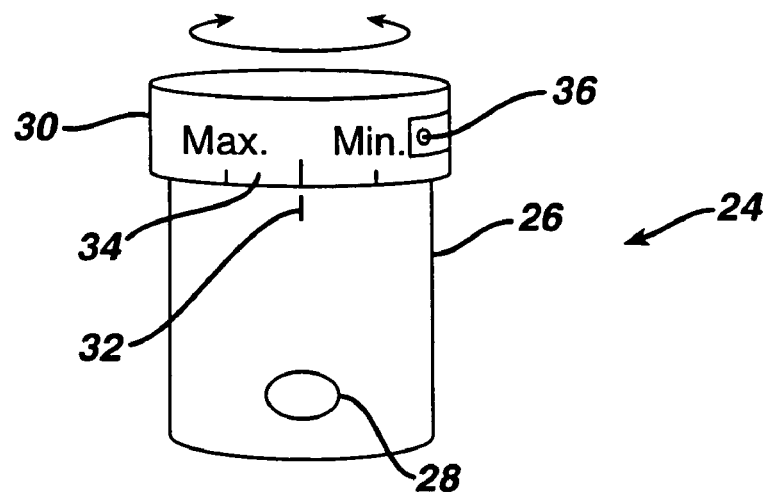
FIG. 2 is a front elevation view of a second embodiment of a process challenge device according to the present invention.

FIG. 2 illustrates a similar process challenge device 24 comprising an enclosure 26 with an indicator 28 therein and it has a cover 30 at one end, which can be rotated into various positions to vary the diffusion restriction into the enclosure 26. An indicator mark 32 and scale 34 are provided on the cover for indicating the amount of diffusion restriction that has been selected. The amount of diffusion restriction should correlate to the ease or difficulty in diffusing the sterilant into devices to be sterilized, and the scale 34 may relate to a feature of the load relevant to such, as for instance the quantity of devices or the length of the most challenging lumen in the load. Preferably, detents are provided between the cover 30 and enclosure 26, or some friction is provided, to keep the cover in the proper position during the procedure. The diffusion restriction in this case can comprise apertures 36 selectively covered and uncovered by the cover 30 but can comprise other restrictions of a variable nature.

Figure 3:
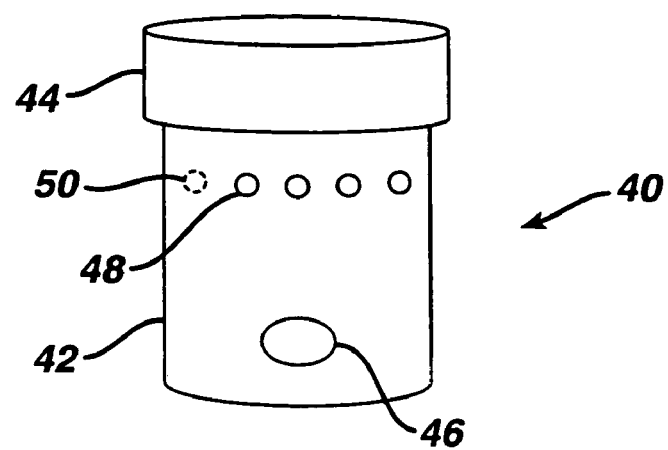
FIG. 3 is a front elevation view of a third embodiment of a process challenge device according to the present invention.

FIG. 3 illustrates a third embodiment of a process challenge device 40 according to the present invention. It comprises a container 42 having a lid 44, and containing an indicator 46. A plurality of apertures 48 provide a diffusion-restricted passage into the container 42. One or more of the apertures are closed initially but may be opened by punching out a disk 50. Preferably, the disk 50 is formed by shaping the surface of the container 42 in the shape of the aperture 48 creating a frangible connection between the disk 50 and the remaining material of container 42.

Figure 4:
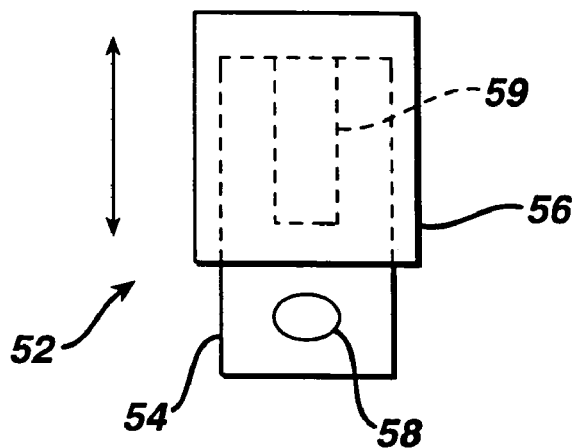
FIG. 4 is a front elevation view of a fourth embodiment of a process challenge device according to the present invention.

The apertures disclosed in the first, second and third embodiments may be the same in size, or may vary in size, with the user preferably punching out or uncovering ever larger apertures to rapidly decrease the diffusion restriction. Especially with the first and second embodiments, the plurality of apertures could be replaced by a single elongated slot. The degree to which it is uncovered determines the diffusion restriction. Such is illustrated in FIG. 4. It discloses a process challenge device 52 similar to the challenge device 10 comprised of first and second bodies 54 and 56 in telescoping relationship and containing therein an indicator 58. Rather than a plurality of apertures, an elongated slot 59 through the first body 54 is fully or partially uncovered through the telescoping relationship of the bodies to determine the diffusion restriction.

Figure 5:
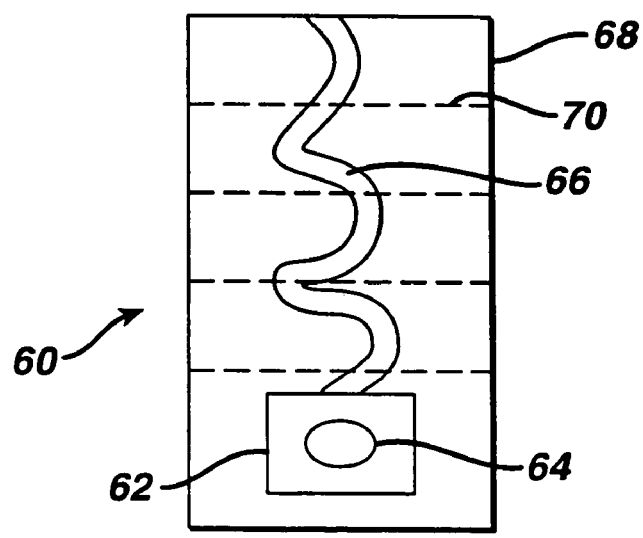
FIG. 5 is a top plan view of a fifth embodiment of a process challenge device according to the present invention.

FIG. 5 illustrates an alternative concept in which a process challenge device 60 comprises a container 62 having an indicator 64 therein and a tortuous path 66 leading to the indicator. Portions 68 of the container 62 can be removed to shorten the tortuous path 66. For instance, if the container is formed of mating polymer sheets with a channel formed therein creating the tortuous path 66, portions of the sheets can be cut off with scissors. Alternatively, the container 62 can be formed of films with an at least partially rigid lumen placed therebetween to form the path 66. Preferably, cut indication lines 70 are provided thereon to indicate particular locations to cut with a specified degree of diffusion restriction remaining.

Not only can the length of the tortuous path 66 be varied; it can be formed of material showing different levels of absorption. Preferably, that portion furthermost away from the indicator 64 would be formed of the most absorbent material and that portion closest to the indicator formed of a low absorption or non-absorptive material. Such materials include certain polymers known to absorb sterilants such as polyesters, polyurethanes, silicones, and nylons, which absorb hydrogen peroxide, or more traditional absorbent materials such as cellulosic materials. Rather than form the path entirely of such absorbent materials, portions of absorbent material can be located in select locations along the path.

FIG. 6 illustrates a further embodiment of a process challenge device 80 comprising an elongated lumen 82 containing an indicator 84 at the closed end 86 thereof. The length of absorbent material 88 is put into the lumen 82 through an opposite open end thereof 90. Preferably, the absorbent material 88 has markings 92 thereon to indicate places where it can be cut or torn to reduce its length and, thus, its absorptive capacity. The process challenge device 80 is disposed within a breathable pouch 94 to provide further diffusion restriction. Any of the embodiments herein can be enclosed in a further diffusion restriction to enhance the challenge they provide.

Each of the disclosed embodiments incorporates some form of indicator. This indicator is preferably a biological indicator such as described in the background thereon but may also comprise an indicator for the presence of a particular sterilant such as a chemical indicator for the presence of hydrogen peroxide or the like. Such indicators are more fully described in U.S. Pat. Nos. 6,218,189 and 6,267,242 incorporated herein by reference. Further, the indicator may be more active, such as a reactive chemical on a thermal couple to detect the presence of a chemical sterilant as disclosed in pending U.S. patent application Ser. No. 09/741,594, filed Dec. 19, 2000, incorporated herein by reference.

FIG. 7 discloses a process challenge device 100 comprising a container 102 having an indicator 104 therein. Elongated lumens 106 and 108 extend laterally from the container 102. Each lumen 106 and 108 has markings 110 thereon to indicate its length. Preferably, each lumen 106 and 108 has an internal diameter of similar diameter to a particular device being processed. For instance, an endoscope having a lumen of 1.5 meters and an internal diameter of 1 millimeter, each of the lumens 106 and 108 would have an internal diameter of 1 mm and a length approximately one-half the length of the actual lumen, or 0.75 m to thus simulate the sterilant diffusing into the center of the device lumen.

In use, an operator would determine a certain characteristic of the load such as the number of instruments, the number of wrapped instrument containers, certain types of materials, which may be absorptive, or the length of any difficult-to-sterilize lumens. This would then correlate to a particular setting on a process challenge device. For instance, using the process challenge device 10, the user may determine that only 30 percent of the apertures 22 should be uncovered to provide a process challenge indicative of the particular load to be sterilized. The devices and the process challenge device 10 are then sterilized in the usual manner. For instance, they may be placed into a steam sterilizer and processed, or into a hydrogen peroxide vapor sterilizer. One such example is the STERRAD® process from Advanced Sterilization Systems in which the devices are placed into a chamber which is evacuated and into which is introduced hydrogen peroxide vapor to sterilize the articles. At some point during the cycle, the hydrogen peroxide vapor is excited into plasma, which has the beneficial effect of leaving behind very few residual hydrogen peroxide molecules. After the procedure is completed, the process challenge device is removed and the indicator examined to assess the efficacy of the sterilization procedure.

It should be noted that the present invention is not limited to only those embodiments described herein. Any embodiment which retains the spirit of the present invention should be considered to be within its scope. The invention is only limited by the scope of the following claims.

What is claimed is:

1. A sterilization process challenge device comprising:
   a sterilization indicator contained within a container; and
   a variable diffusion restriction into said container,
   wherein the variable diffusion restriction comprises a diffusion path into said container, and the diffusion path comprises an adjustable covering for said path to block or unblock a portion of said diffusion path and wherein the container comprises a first member and a second member disposed in telescoping relation with a plurality of openings disposed on the first member and the second member forming the adjustable covering.

2. A sterilization process challenge device according to claim 1 wherein the sterilization indicator is a biological indicator.

3. A sterilization process challenge device according to claim 1 wherein the sterilization indicator is a chemical indicator indicative of a chemical sterilant.

4. A sterilization process challenge device according to claim 1 wherein the diffusion path comprises a plurality of openings.

5. A sterilization process challenge device according to claim 4 wherein openings are different in size.

6. A sterilization process challenge device according to claim 4 wherein at least one opening is covered with a removable covering.

7. A sterilization process challenge device according to claim 1 wherein the diffusion path comprises a slot.

8. A sterilization process challenge device according to claim 1 wherein the diffusion path comprises a long narrow path, wherein the diffusion path can be adjusted by trimming the length of the path.

9. A sterilization process challenge device according to claim 8 wherein the diffusion path comprises at least two materials wherein said materials have different capabilities to retain sterilant.

10. A sterilization process challenge device according to claim 1 wherein the diffusion path further comprises a sterilant absorber such that the amount of sterilant diffusing to the indicator can be adjusted by the type or the size of the absorber.

11. A method for assessing the sterilization efficacy of a sterilization process comprising the steps of:
    Placing a sterilization process challenge device in proximity to a device to be sterilized during the sterilization process, the sterilization process challenge device comprising a container, a sterilization indicator within the container, an opening into said container and an adjustable diffusion restriction at said opening;
    assessing a feature of a load of one or more device to be sterilized in said sterilization process;
    adjusting the amount of diffusion restriction provided by said diffusion restriction based upon said feature of said load; and
    indicating the sterilization efficacy with the indicator,
    wherein the step of adjusting the amount of diffusion restriction comprises adjusting an area of the opening into the container and wherein the area of opening into the container is adjusted by covering and uncovering the opening into the container.

12. A method according to claim 11 wherein the opening comprises a plurality of apertures in a wall of the container.

13. A method according to claim 11 wherein the diffusion restriction comprises a path into the container and the step of adjusting the amount of diffusion restriction comprises adjusting the length of the path.

14. A method according to claim 11 wherein the step of adjusting the diffusion restriction comprises adjusting an amount of absorbent material placed adjacent the indicator.

15. A method according to claim 11 wherein the indicator indicates whether a reference organism remains viable.

16. A method according to claim 11 wherein the indicator indicates whether a sufficient amount of a sterilizing gas was present during the sterilization process.

* * * * *